(12) United States Patent
Coats

(10) Patent No.: US 10,842,467 B2
(45) Date of Patent: Nov. 24, 2020

(54) BIOSPECIMEN EXTRACTION APPARATUS

(71) Applicant: Portal Instruments, Inc., Cambridge, MA (US)

(72) Inventor: Andrew Coats, Somerville, MA (US)

(73) Assignee: Portal Instruments, Inc., Cambridge, MA (US)

( * ) Notice: Subject to any disclaimer, the term of this patent is extended or adjusted under 35 U.S.C. 154(b) by 607 days.

(21) Appl. No.: 15/378,205

(22) Filed: Dec. 14, 2016

(65) Prior Publication Data

US 2017/0164933 A1    Jun. 15, 2017

Related U.S. Application Data

(60) Provisional application No. 62/267,339, filed on Dec. 15, 2015.

(51) Int. Cl.
| | | |
|---|---|---|
| *A61B 5/00* | (2006.01) | |
| *A61B 10/00* | (2006.01) | |
| *A61B 10/02* | (2006.01) | |

(52) U.S. Cl.
CPC .......... *A61B 10/0045* (2013.01); *A61B 10/02* (2013.01); *A61B 2010/008* (2013.01)

(58) Field of Classification Search
CPC ........ G16H 50/30; G16H 10/40; G01N 33/49; A61B 10/0283; A61B 17/32002; A61B 17/32053; A61B 18/042; A61B 2017/00398; A61B 5/489
USPC ........ 600/573, 575–578; 604/68, 70, 71, 73, 604/131, 72; 606/170
See application file for complete search history.

(56) References Cited

U.S. PATENT DOCUMENTS

| | | | | | |
|---|---|---|---|---|---|
| 5,199,949 | A | * | 4/1993 | Haber | A61M 5/19 604/191 |
| 6,056,716 | A | * | 5/2000 | D'Antonio | A61M 5/24 604/134 |
| 6,224,567 | B1 | * | 5/2001 | Roser | A61M 5/28 604/218 |
| 7,833,189 | B2 | * | 11/2010 | Hunter | A61B 17/20 604/68 |
| 7,867,174 | B2 | * | 1/2011 | Rivet | A61B 5/14 600/573 |
| 8,066,662 | B2 | * | 11/2011 | Azar | A61M 5/204 604/70 |
| 8,328,755 | B2 | * | 12/2012 | Hunter | A61B 17/20 604/68 |
| 8,398,583 | B2 | * | 3/2013 | Hunter | A61B 10/0045 604/68 |
| 8,740,838 | B2 | * | 6/2014 | Hemond | A61M 5/30 604/68 |
| 8,821,434 | B2 | * | 9/2014 | Hunter | A61M 5/30 604/70 |

(Continued)

*Primary Examiner* — May A Abouelela
(74) *Attorney, Agent, or Firm* — Occhiuti & Rohlicek LLP

(57) ABSTRACT

Needle-less extraction of a biospecimen from tissue having a number of tissue layers including an epidermis layer includes creating a first port through a target surface and into an underlying one of the tissue layers, creating a second port through the target surface and into the underlying one of tissue layers, providing an injectate through the first port to the underlying one of the tissue layers underlying the epidermis layer, and extracting at least a portion of the injectate and the biospecimen from the underlying one of the layers through the second port.

19 Claims, 10 Drawing Sheets

(56) References Cited

U.S. PATENT DOCUMENTS

| | | | | |
|---|---|---|---|---|
| 8,905,966 B2* | 12/2014 | Yoh | ............... | A61M 5/30 604/140 |
| 8,998,881 B2* | 4/2015 | Gilbert | ............... | A61M 5/30 604/521 |
| 9,987,037 B2* | 6/2018 | Hunter | ............... | A61B 17/3203 |
| 2002/0007143 A1* | 1/2002 | Gordon | ............... | A61B 17/3203 604/70 |
| 2002/0188250 A1* | 12/2002 | Landau | ............... | A61M 5/30 604/70 |
| 2004/0260234 A1* | 12/2004 | Srinivasan | ............... | A61M 5/30 604/66 |
| 2005/0187516 A1* | 8/2005 | Neracher | ............... | A61M 5/30 604/68 |
| 2005/0209554 A1* | 9/2005 | Landau | ............... | A61M 5/30 604/72 |
| 2006/0089594 A1* | 4/2006 | Landau | ............... | A61M 5/30 604/68 |
| 2006/0184101 A1* | 8/2006 | Srinivasan | ............... | A61M 25/0069 604/68 |
| 2006/0258986 A1* | 11/2006 | Hunter | ............... | A61D 7/00 604/164.01 |
| 2006/0264808 A1* | 11/2006 | Staid | ............... | A61M 1/0084 604/22 |
| 2007/0043320 A1* | 2/2007 | Kenany | ............... | A61M 37/00 604/68 |
| 2007/0055214 A1* | 3/2007 | Gilbert | ............... | A61M 5/30 604/500 |
| 2007/0191758 A1* | 8/2007 | Hunter | ............... | A61B 17/20 604/22 |
| 2008/0009788 A1* | 1/2008 | Hunter | ............... | A61M 5/3007 604/68 |
| 2009/0137926 A1* | 5/2009 | Srinivasan | ............... | A61M 5/30 600/562 |
| 2009/0247905 A1* | 10/2009 | Rivet | ............... | A61B 5/14 600/573 |
| 2009/0292239 A1* | 11/2009 | Hansen | ............... | A61M 5/19 604/72 |
| 2011/0046600 A1* | 2/2011 | Crank | ............... | A61M 25/0068 604/500 |
| 2011/0082388 A1* | 4/2011 | Hunter | ............... | A61B 10/0045 600/573 |
| 2011/0230826 A1* | 9/2011 | Yoh | ............... | A61M 5/30 604/70 |
| 2012/0157965 A1* | 6/2012 | Wotton | ............... | A61K 9/0019 604/506 |
| 2013/0066263 A1* | 3/2013 | Yoh | ............... | A61M 5/30 604/70 |
| 2015/0157809 A1* | 6/2015 | Park | ............... | A61M 5/204 604/131 |
| 2015/0265770 A1* | 9/2015 | Yoh | ............... | A61M 35/00 604/70 |
| 2015/0289894 A1* | 10/2015 | Miyazaki | ............... | A61B 17/3203 606/170 |
| 2015/0335343 A1* | 11/2015 | Hunter | ............... | A61B 17/3203 606/170 |

* cited by examiner

BIOSPECIMEN EXTRACTION APPARATUS

CROSS REFERENCE TO RELATED APPLICATIONS

This application claims priority to U.S. application Ser. No. 62/267,339, filed on Dec. 15, 2015, the contents of which are incorporated herein by reference.

BACKGROUND

This invention relates to a biospecimen extraction apparatus and a method for biospecimen extraction.

Conventional biospecimen extraction techniques (e.g., interstitial fluid extraction techniques) often use invasive and painful tools such as needles to puncture the skin of a patient for the purpose of biospecimen extraction.

SUMMARY

In a general aspect, a needle-free method of extracting interstitial fluid from upper tissue layers for diagnostic purposes uses two needle-free ports. Two jets originating from the two ports create a port for an injectable fluid to pass into the skin and to create a second port for the injectable fluid, intermingled with a biospecimen, to be ejected or passed back out of the skin.

In another general aspect, a method for needle-less extraction of a biospecimen from tissue having a number of tissue layers including an epidermis layer includes creating a first port through a target surface and into an underlying one of the number of tissue layers, creating a second port through the target surface and into the underlying one of number of tissue layers, providing an injectate through the first port to the underlying one of the number of tissue layers underlying the epidermis layer, and extracting at least a portion of the injectate and the biospecimen from the underlying one of the layers through the second port.

Aspects may include one or more of the following features.

Creating the first port and creating the second port may occur substantially simultaneously. The first port may be created at a first depth relative to a surface of the epidermis and the second port may be created at a second depth relative to the surface of the epidermis. The first depth and second depth may be substantially the same. The first port may be created at a first angle relative to the target surface and the second port may be created at a second angle relative to the target surface. The number of the tissue layers may include a dermis layer and a subcutaneous layer underlying the epidermis layer.

The underlying one of the number of tissue layers may be in the dermis layer. The underlying one of the number of tissue layers may be in the subcutaneous layer. Creating the first port may include using a first needle-less injection device and creating the second port may include using a second needle-less injection device. Creating the first port and creating the second port may occur substantially simultaneously. Creating the first port may include using the first needle-less injection device and creating the second port may include using the first needle-less injection device.

The method may include, after creating the first port with the first needle-less injection device, moving the first needle-less injection device, followed by creating the second port with the first needle-less injection device. The biospecimen may be a fluid. The fluid may be an extracellular fluid or a cerebrospinal fluid. Tissue may be selected from a group consisting of muscle, cartilage, and organ. The injectate may be a fluid. The fluid may be gaseous.

In another general aspect, a needle-less biospecimen extraction apparatus includes a housing having a distal end, one or more chambers disposed within the housing. Each chamber of the one or more chambers has a plunger disposed therein. A first opening is disposed in the distal end of the housing and is in fluid communication with a chamber of the one or more chambers via a first channel. A second opening is disposed in the distal end of the housing and is in fluid communication with a chamber of the one or more chambers via a second channel. The second opening is spatially separated from the first opening by a first distance and the second channel is arranged at an angle relative to the first channel. The first distance and the angle determine a second distance from the distal end of the housing at which a first jet of fluid ejected from the first opening intersects with a second jet of fluid ejected from the second opening. The apparatus also includes an actuator mechanism for moving the plunger of each chamber of the one or more chambers along a length of the chamber and a controller for controlling the actuator mechanism to move the plunger of each chamber of the one or more chambers according to a biospecimen extraction profile.

Aspects may include one or more of the following features.

The one or more chambers may include a first chamber in fluid communication with the first opening via the first channel and a second chamber in fluid communication with the second opening via the second channel. The one or more chambers may include a first chamber in selective fluid communication with the first opening via the first channel and in selective fluid communication with the second chamber via the second channel. The apparatus may further include a valve for placing one of the openings into fluid communication with the first chamber and for preventing fluid communication of the other of the openings and the first chamber.

Other features and advantages of the invention are apparent from the following description, and from the claims.

DESCRIPTION

Figure 1:
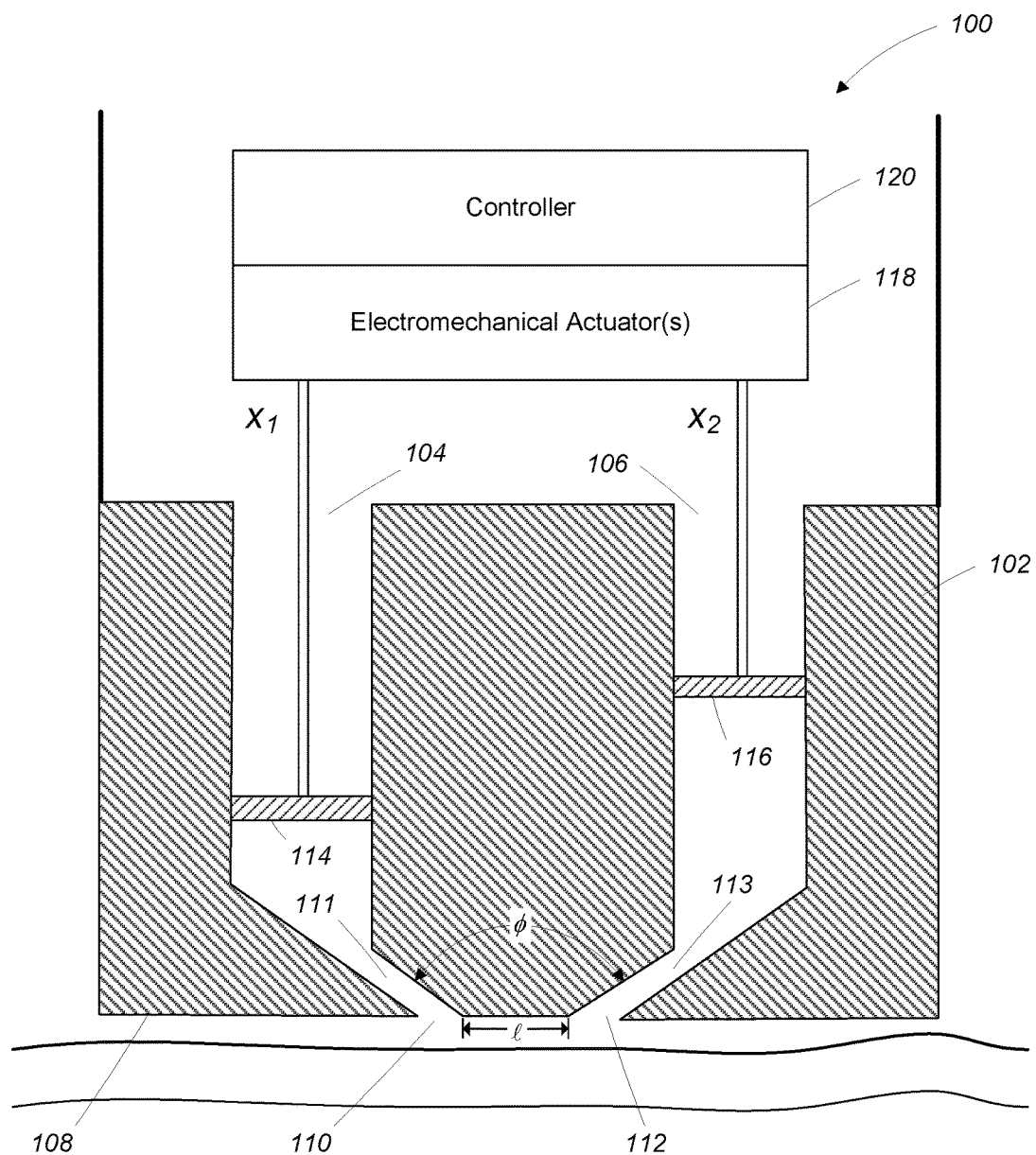
FIG. 1 is a schematic diagram of a first biospecimen extraction apparatus.

Referring to FIG. 1, a needle-free biospecimen extraction apparatus 100 is configured to extract a biospecimen from a patient without the use of needles or other invasive sampling devices.

The apparatus 100 includes a housing 102 having a first chamber 104 and a second chamber 106 disposed therein. A distal end 108 of the housing 102 includes a first opening 110 that is in fluid communication with the first chamber 104 via a first channel 111 and a second opening 112 that is in fluid communication with the second chamber 106 via a second channel 113. It is noted that a distance, $\zeta$ exists between the first opening 110 and the second opening 112, and an angle, $\varphi$ exists between the first channel 111 and the second channel 113. The distance, $\zeta$ and the angle, $\varphi$ are specified to ensure that jets of fluid ejected from the first opening 110 and the second opening 112 intersect at a predetermined depth under a target surface (e.g., the epidermis) on a patient's skin.

The first chamber 104 has a first plunger 114 disposed therein and the second chamber 106 has a second plunger 116 disposed therein. The first plunger 114 and the second plunger 116 are independently movable along the lengths of their respective chambers 104, 106 by one or more electromechanical actuators 118 (e.g., linear actuators). A direction and speed of the movement of the plungers 114, 116 is controlled by a controller 120 according to a biospecimen extraction displacement profile.

Figure 2:
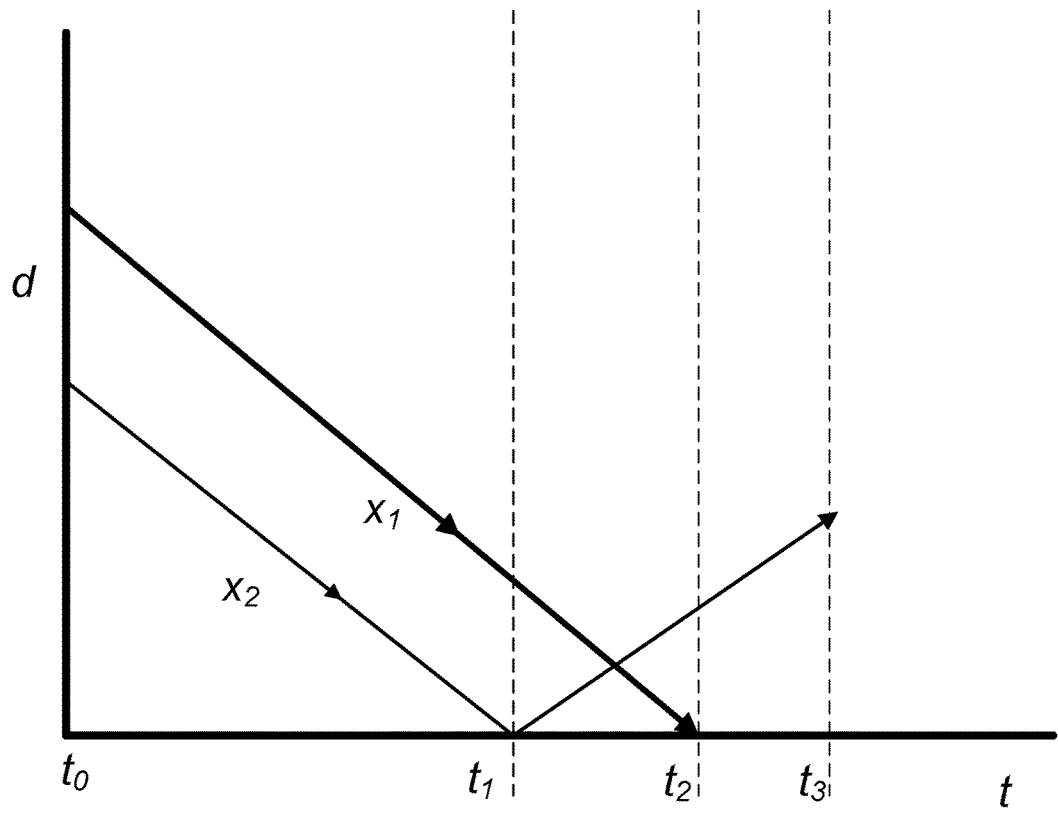
FIG. 2 is a biospecimen extraction profile for the biospecimen extraction apparatus of FIG. 1.

Referring to FIG. 2, one example of a biospecimen extraction displacement profile 200 shows a displacement of both the first plunger (i.e., $X_1$) 114 and the second plunger (i.e., $X_2$) 116 over time. According to the displacement profile 200 of FIG. 2, the controller 120 controls the plungers 114, 116 through three stages, a first stage from times $t_0$ to $t_1$, a second stage from times $t_1$ to $t_2$, and a third stage from times $t_2$ to $t_3$.

Figure 3:
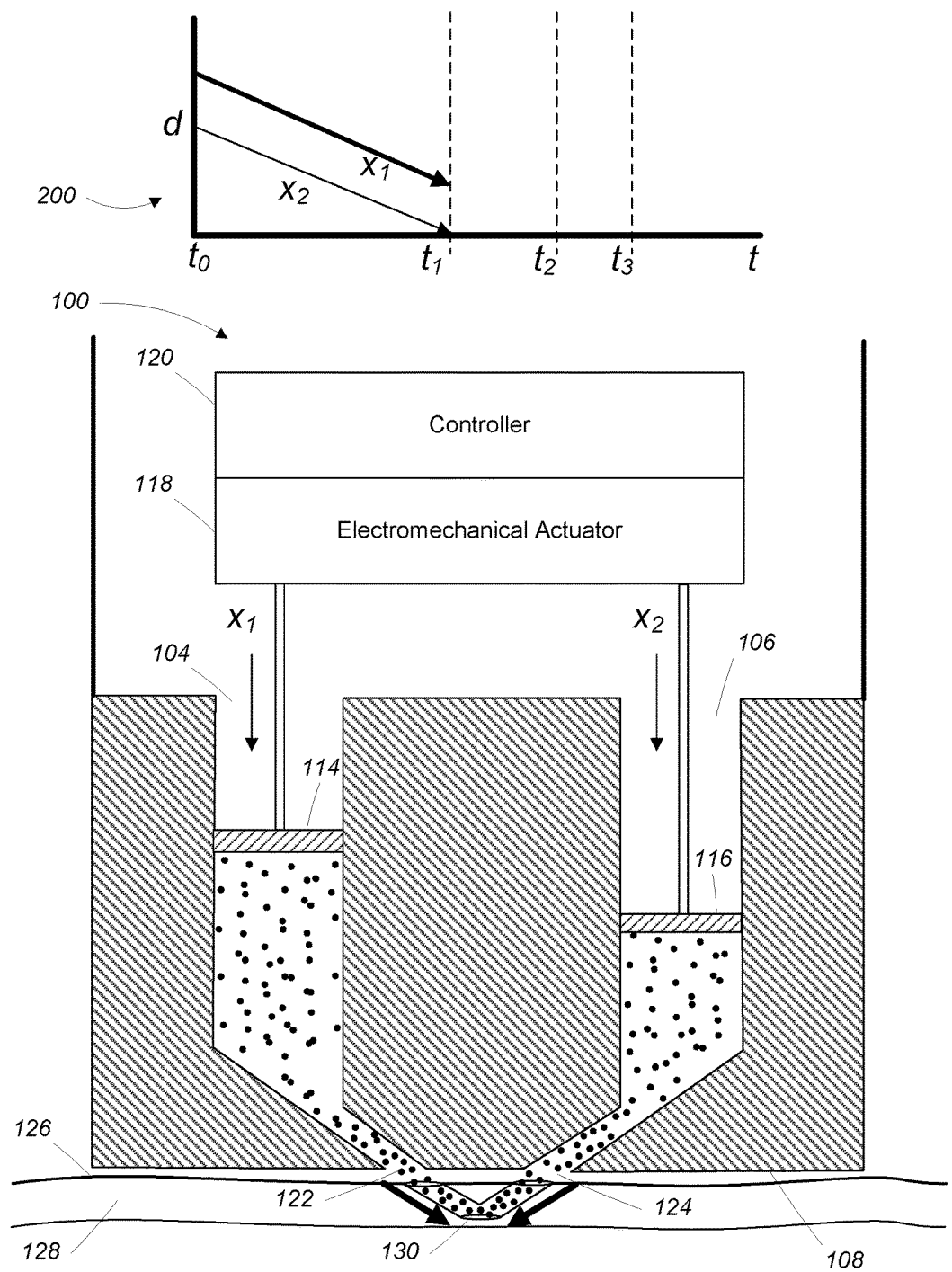
FIG. 3 shows the biospecimen extraction apparatus of FIG. 1 performing the first step of the biospecimen extraction profile of FIG. 2.

Referring to FIG. 3, during the first stage of the displacement profile 200, at a time to the plungers 114, 116 are at a starting displacement in their respective chambers 104, 106. The controller 120 causes the electromechanical actuator(s) 118 to move both of the plungers 114, 116 toward the distal end 108 of the housing 102, thereby causing ejection of any fluid in the chambers 104, 106 (e.g., air or a liquid such as saline) out of the chambers via the openings 110, 112. The ejection of fluid through openings 110, results in two jets 122, 124 of fluid which pierce an epidermis 126 of the patient's skin and intersect at a predetermined depth underneath the patient's skin (in this case, in the dermal layer 128). At the conclusion of the first stage, $t_1$, a port 130 is established between the first opening 110 and the second opening 112 via the patient's epidermis 126 and dermal layer 128.

Figure 4:
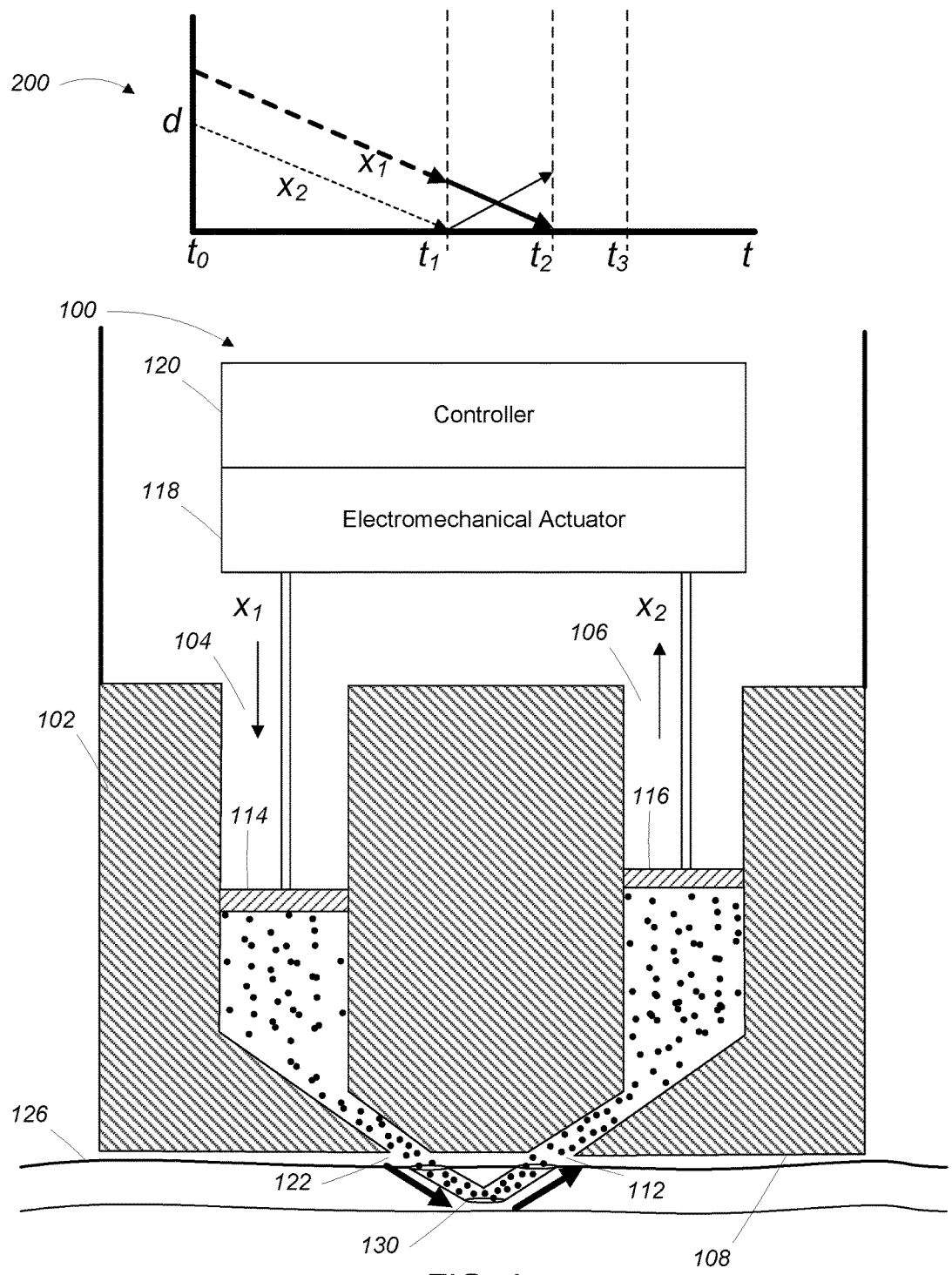
FIG. 4 shows the biospecimen extraction apparatus of FIG. 1 performing the second step of the biospecimen extraction profile of FIG. 2.

Referring to FIG. 4, at the beginning of the second stage of the displacement profile 200 (i.e., at time $t_1$), the controller 120 causes the electromechanical actuator(s) 118 to continue moving the first plunger 114 in a direction toward the distal end 108 of the housing 102 but reverses the direction of the second plunger 116 such that it moves in a direction away from the distal end 108 of the housing 102. This causes the first jet of fluid 122 to continue to force fluid into the port 130. The reversal of the movement of the second plunger 116 causes the second jet of fluid 124 to stop flowing and creates a vacuum at the second opening 112. The combination of the first jet 122 flowing out of the first opening 110 into the port 130 and the vacuum at the second opening 112 causes fluid to be drawn through the port 130 and into the second chamber 106. As the fluid is drawn through the port 130, it intermingles with a biospecimen (e.g., interstitial fluid) such that the fluid drawn into the second chamber 106 includes the biospecimen.

Figure 5:
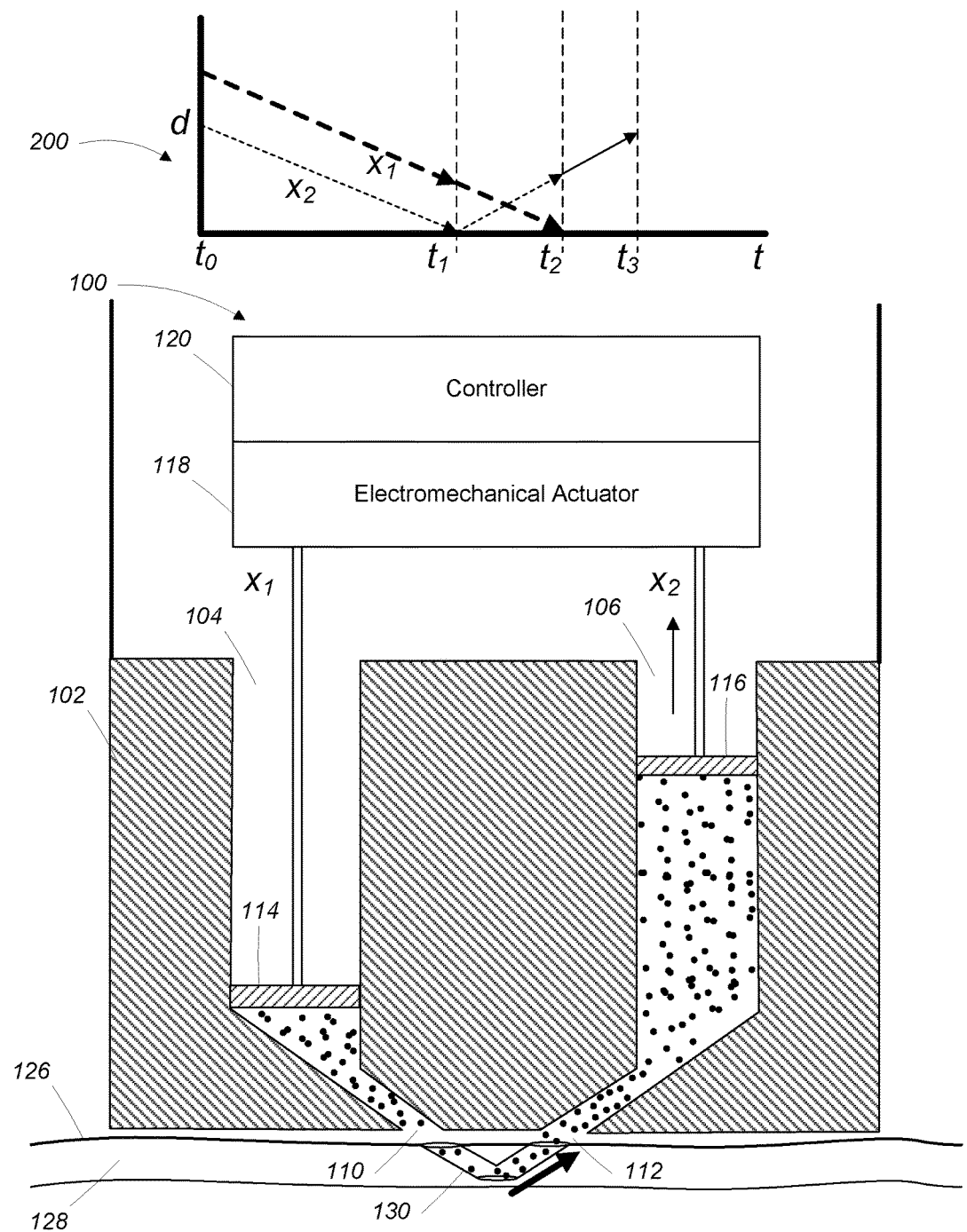
FIG. 5 shows the biospecimen extraction apparatus of FIG. 1 performing the third step of the biospecimen extraction profile of FIG. 2.

Referring to FIG. 5, at the beginning of the third stage of the displacement profile 200 (i.e., at time $t_2$), the controller 120 stops movement of the first plunger 116 in the first chamber 104 and continues movement of the second plunger 116 in a direction away from the distal end 108 of the housing, thereby drawing an additional amount of biospecimen from the patient.

Figure 6:
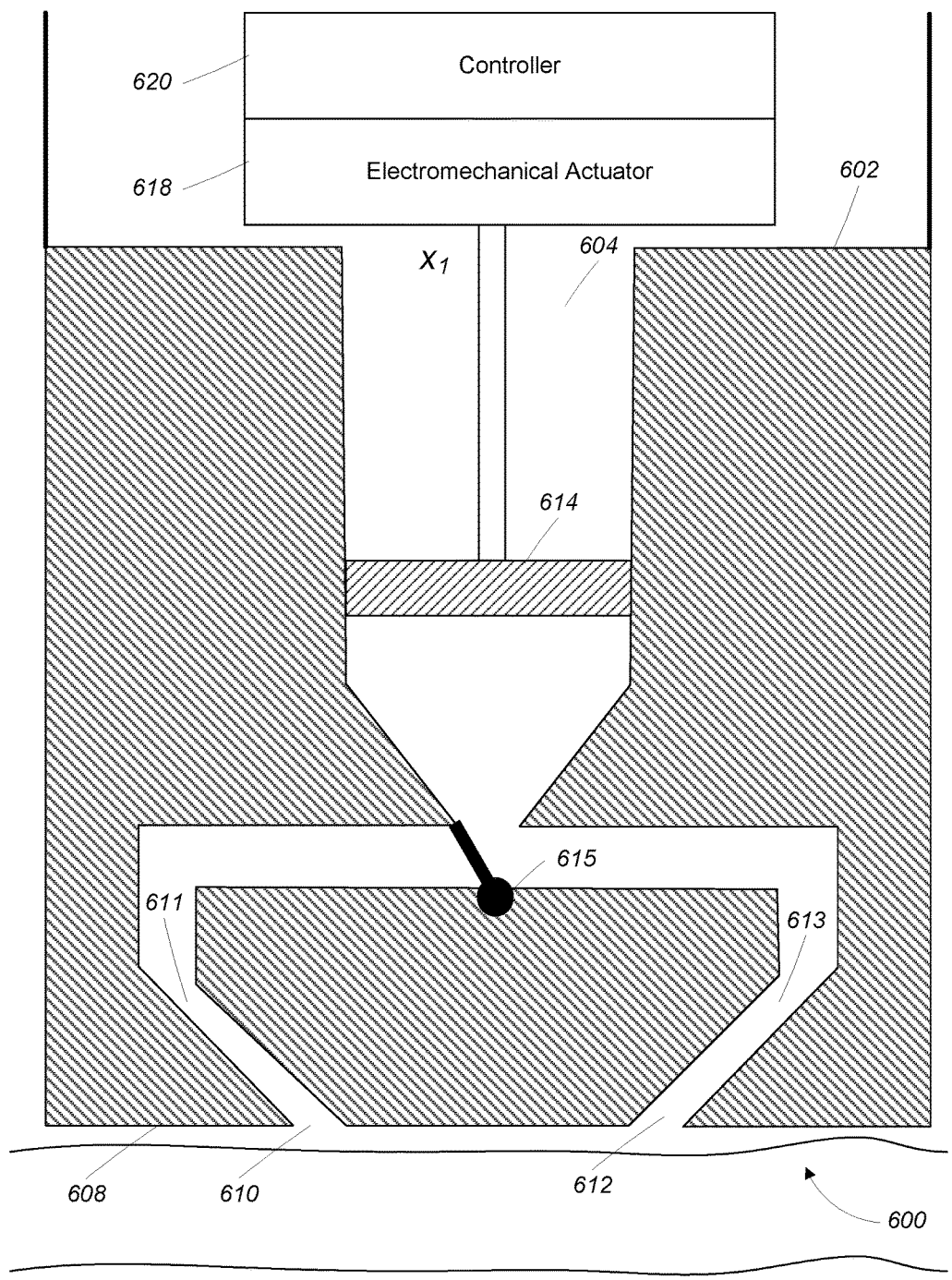
FIG. 6 is a schematic diagram of a second biospecimen extraction apparatus.

Referring to FIG. 6, another embodiment of a needle-free biospecimen extraction apparatus 600 is configured to extract a biospecimen from a patient without the use of needles or other invasive sampling devices.

The apparatus 600 includes a housing 602 having a chamber 604 disposed therein. A distal end 608 of the housing 602 includes a first opening 610 that is in fluid communication with the chamber 604 via a first channel 611 and a second opening 612 that is in fluid communication with the chamber 604 via a second channel 613. It is noted that a distance, $\zeta$ exists between the first opening 610 and the second opening 612, and an angle, $\varphi$ exists between the first channel 611 and the second channel 613. The distance, $\zeta$ and the angle, $\varphi$ are specified to ensure that jets of fluid ejected from the first opening 610 and the second opening 612 intersect at a predetermined depth under the surface of a patient's skin. A flap (or valve) 615 is disposed at an outlet of the chamber 604 and is controlled (e.g., by a controller 620) to establish fluid communication between one of the channels 611, 613 and the chamber 604 and to block fluid communication between the other of the channels 611, 613 and the chamber 604. That is, the flap 615 causes only one of the channels 611, 613 to be in fluid communication with the chamber 604 at a time.

The chamber 604 has a plunger 614 disposed therein. The plunger 614 movable along the length of the chamber 604 by one or more electromechanical actuators 618 (e.g., linear actuators). A direction and speed of the movement of the plunger 614 is controlled by the controller 620 according to a biospecimen extraction displacement profile.

Figure 7:
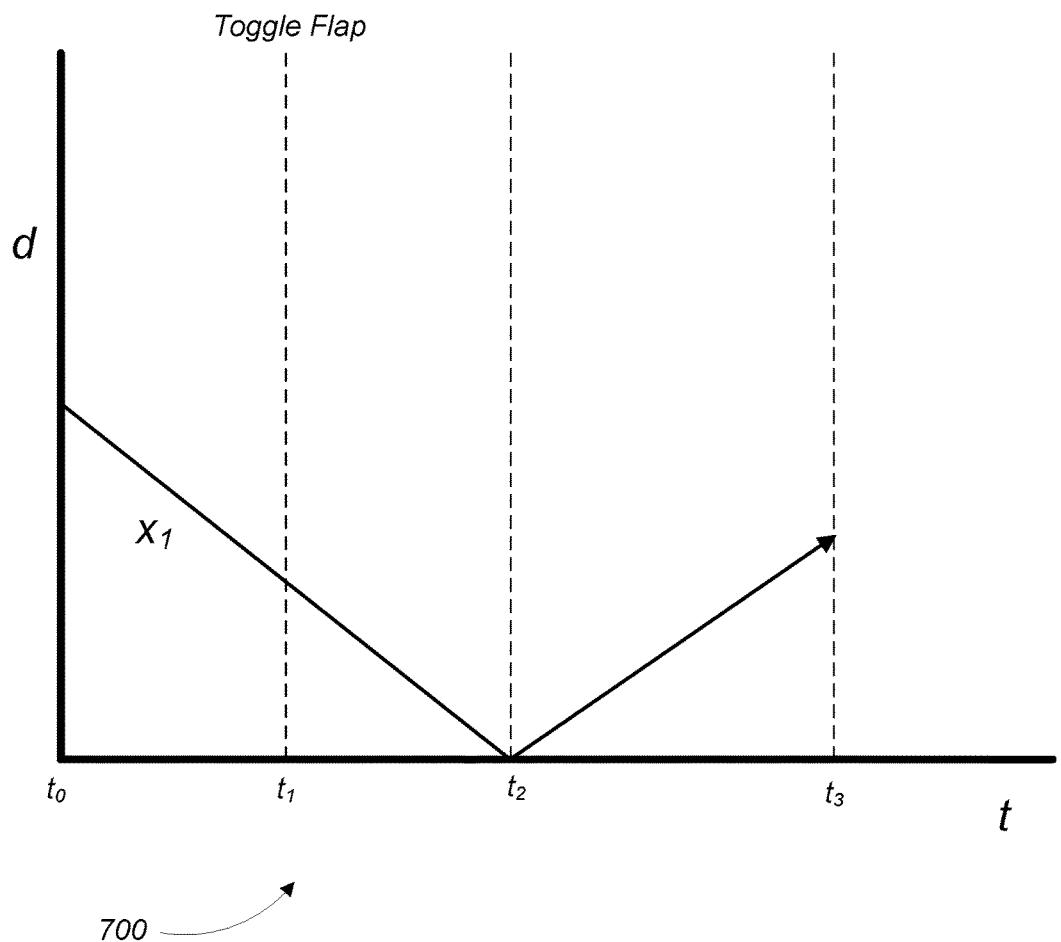
FIG. 7 is a biospecimen extraction profile for the biospecimen extraction apparatus of FIG. 6.

Referring to FIG. 7, one example of a biospecimen extraction displacement profile 700 shows a displacement of the first plunger 614 (i.e., $X_1$) over time. According to the displacement profile 700 of FIG. 7, the controller 620 controls the plunger 614 through three stages, a first stage from times $t_0$ to $t_1$, a second stage from times $t_1$ to $t_2$, and a third stage from times $t_2$ to $t_3$.

Figure 8:
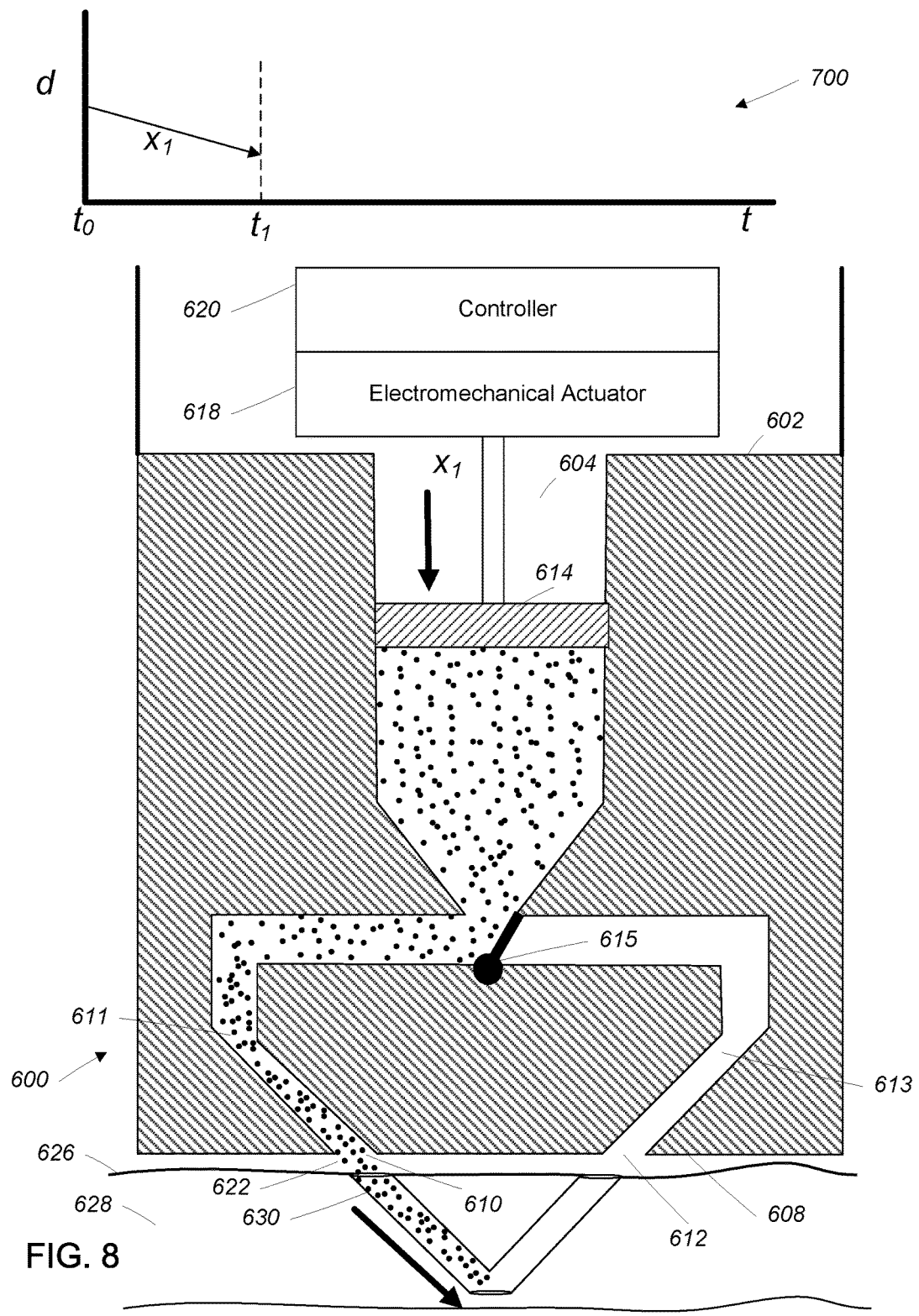
FIG. 8 shows the biospecimen extraction apparatus of FIG. 6 performing the first step of the biospecimen extraction profile of FIG. 7.

Referring to FIG. 8, during the first stage of the displacement profile 700, at a time to the plunger 614 is at a starting displacement in the chamber 604. The flap 615 is positioned such that the first channel 611 and the first opening 610 are in fluid communication with the chamber 604 and fluid communication between the second channel 613, the second opening 612, and the chamber 604 is blocked.

The controller 620 causes the electromechanical actuator(s) 618 to move the plunger 614 toward the distal end 608 of the housing 602, thereby causing ejection of fluid in the chamber 604 (e.g., air or a liquid such as saline) out of the chamber 604 via the first opening 610. The ejection of fluid through the first opening 610 results in a jet 622 of fluid which pierces an epidermis 626 of the patient's skin, and creates a first part of a port 630 into the patient's dermal layer 628. At the conclusion of the first stage, $t_1$, the first part of the port 630 is established.

Figure 9:
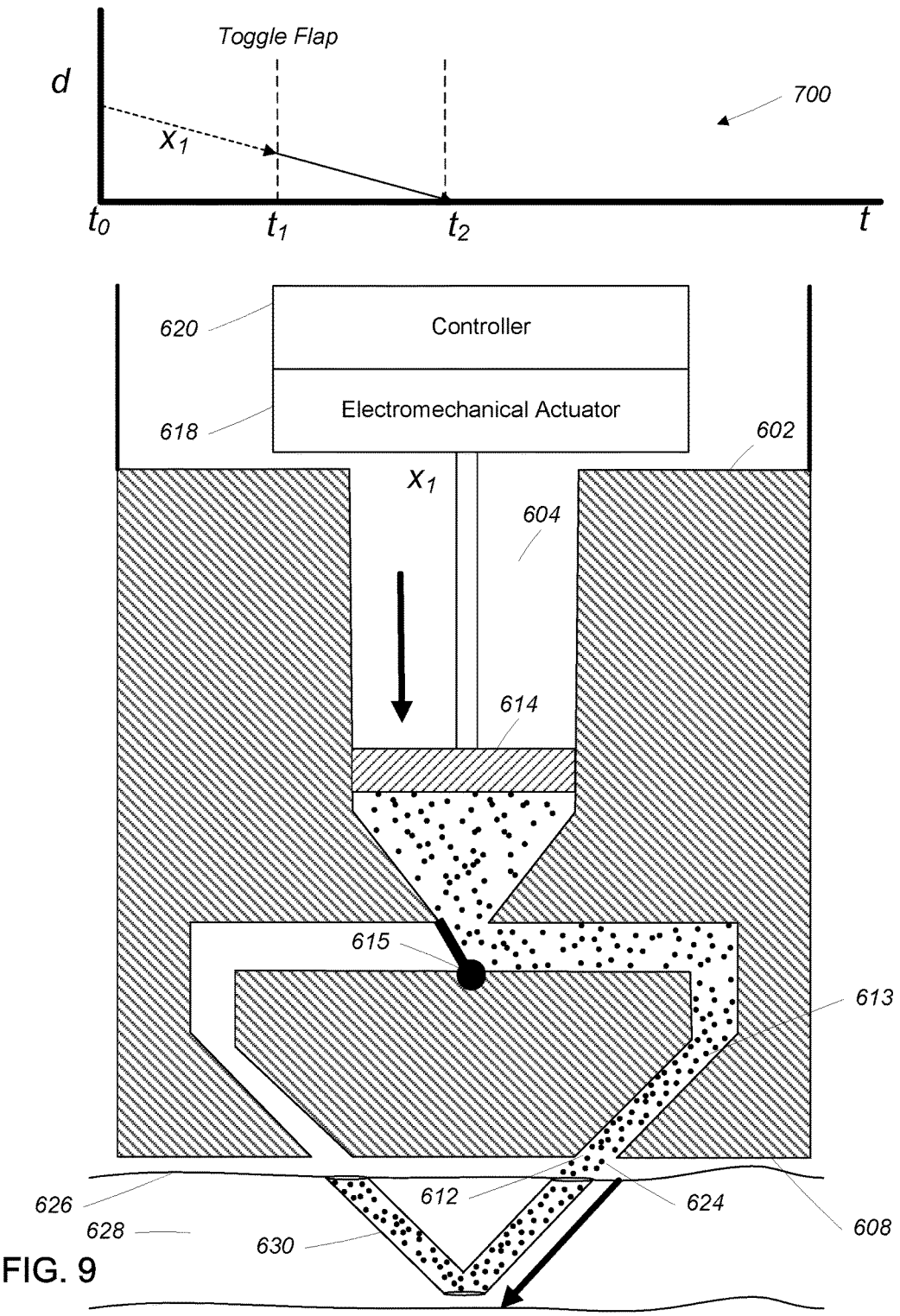
FIG. 9 shows the biospecimen extraction apparatus of FIG. 6 performing the second step of the biospecimen extraction profile of FIG. 7.

Referring to FIG. 9, during the second stage of the displacement profile 700, at time $t_1$ the flap 615 is repositioned (e.g., by the controller 620) such that the second channel 613 and the second opening 612 are in fluid communication with the chamber 604 and fluid communication between the first channel 611, the first opening 610, and the chamber 604 is blocked.

The controller 620 continues to cause the electromechanical actuator(s) 618 to move the plunger 614 toward the distal end 608 of the housing 602, thereby causing ejection of fluid in the chamber 604 out of the chamber 604 via the second opening 612. The ejection of fluid through the second opening 612 results in a jet 624 of fluid which pierces the epidermis 626 of the patient's skin and creates a second part of the port 630 into the patient's dermal layer 628. At the conclusion of the second stage, $t_2$ the port 630 between the first opening 610 and the second opening 612 via the patient's epidermis 626 and dermal layer 628 is fully established.

Figure 10:
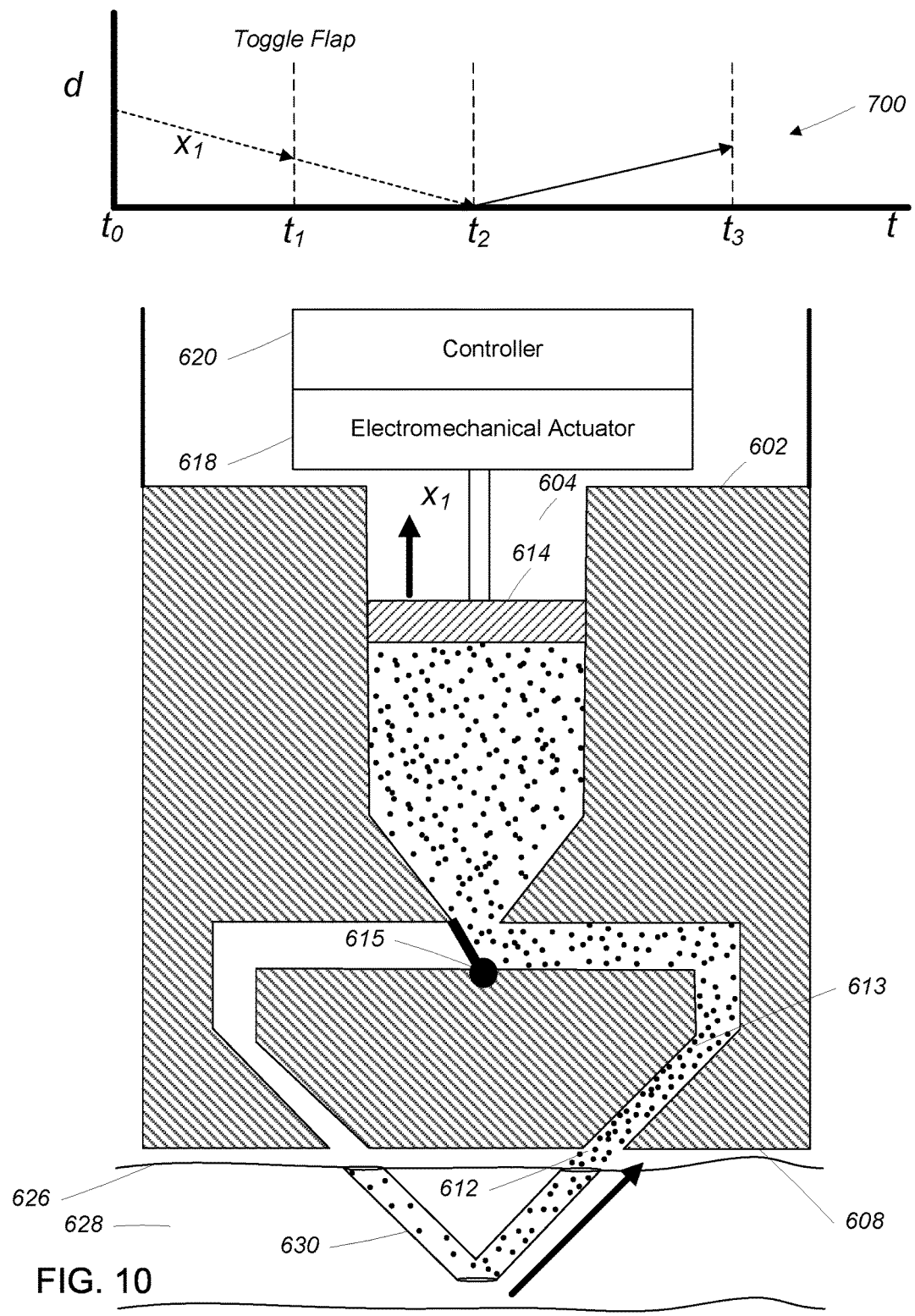
FIG. 10 shows the biospecimen extraction apparatus of FIG. 6 performing the third step of the biospecimen extraction profile of FIG. 7.

Referring to FIG. 10, during the third stage of the displacement profile 700, the controller 620 causes the electromechanical actuator(s) 618 to reverse the direction of the plunger 614 such that it moves in a direction away from the distal end 608 of the housing 602. This creates a vacuum at the second opening 612 which in turn causes fluid to be drawn through the port 630 and into the chamber 604. As the fluid is drawn through the port 630, it intermingles with a biospecimen (e.g., interstitial fluid) such that the fluid drawn into the chamber 604 includes the biospecimen.

ALTERNATIVES

In the examples described above, the angle between the device's channels and the distance between the device's openings are configured such that a port is established through the patient's epidermis and dermal layer. However, it is noted that other configurations of the angle between the device's channels and the distance between the device's openings may be used to achieve ports with different depths into the patient's skin. For example, certain configurations may cause the port to extend into the patient's subcutaneous space or into the patient's muscle.

In some examples, the device may be used to obtain cerebrospinal fluid in a needle-free manner.

In some examples, suction is used to extract the biospecimen from the port in the patient's tissue. In other examples, the biospecimen is ejected from the port in the patient's skin and is collected.

It is to be understood that the foregoing description is intended to illustrate and not to limit the scope of the invention, which is defined by the scope of the appended claims. Other embodiments are within the scope of the following claims.

What is claimed is:

1. A method for needle-less extraction of a biospecimen from tissue having a plurality of tissue layers including an epidermis layer, the method comprising:

causing a first plunger to inject a first fluid jet through a target surface and into an underlying one of the plurality of tissue layers, the first fluid jet including an injectate;

causing a second plunger to inject a second fluid jet through the target surface and into the underlying one of plurality of tissue layer, the second fluid jet being spaced from the first fluid jet along the target surface and intersecting the first fluid jet at a predetermined depth underlying one of the plurality of tissue layers underlying the epidermis layer, whereby the injectate with the first fluid jet is provided to the underlying one of the plurality of tissue layers underlying the epidermis layer; and while causing the first plunger to continue to inject the first fluid jet, causing the second plunger to extract at least a portion of the injectate and the biospecimen from the underlying one of the layers using the second fluid jet.

2. The method of claim 1 wherein injecting the first fluid jet and injecting the second fluid jet occurs substantially simultaneously.

3. The method of claim 1 wherein injecting the first fluid jet is at a first depth relative to a surface of the epidermis and injecting the second fluid jet is at a second depth relative to the surface of the epidermis.

4. The method of claim 3 wherein the first depth and second depth are substantially the same.

5. The method of claim 1 wherein injecting the first fluid jet at a first angle relative to the target surface and injecting the second fluid jet at a second angle relative to the target surface.

6. The method of claim 1 wherein the plurality of the tissue layers includes a dermis layer and a subcutaneous layer underlying the epidermis layer.

7. The method of claim 6 wherein the underlying one of the plurality of tissue layers is in the dermis layer.

8. The method of claim 6 wherein the underlying one of the plurality of tissue layers is in the subcutaneous layer.

9. The method of claim 1 wherein injecting the first fluid jet includes using a first needle-less injection device and injecting the second fluid jet includes using a second needle-less injection device.

10. The method of claim 9 wherein injecting the first fluid jet and injecting the second fluid jet occurs substantially simultaneously.

11. The method of claim 1 wherein injecting the first fluid jet includes using a first needle-less injection device and injecting the second fluid jet includes using the first needle-less injection device.

12. The method of claim 11 further comprising after injecting the first fluid jet with the first needle-less injection device, moving the first needle-less injection device, followed by injecting the second fluid jet with the first needle-less injection device.

13. The method of claim 1 wherein the biospecimen is a fluid.

14. The method of claim 13 wherein the fluid is an extracellular fluid or cerebrospinal fluid.

15. The method of claim 1 wherein the tissue is selected from a group consisting of muscle, cartilage, and organ.

16. The method of claim 1 wherein the injectate is a fluid.

17. The method of claim 16 the fluid is gaseous.

18. The method of claim 5 wherein the first angle relative to the target surface is different than the second angle relative to the target surface.

19. A method for needle-less extraction of a biospecimen from tissue having a plurality of tissue layers including an epidermis layer, the method comprising:

injecting, through a first opening of a needle-less biospecimen extraction apparatus, a first fluid jet through a target surface and into an underlying one of the plurality of tissue layers, the first fluid jet including an injectate;

injecting, through a second opening of the needle-less biospecimen extraction apparatus, a second fluid jet through the target surface and into the underlying one of plurality of tissue layer, the second fluid intersecting the first fluid jet at a predetermined depth underlying one of the plurality of tissue layers underlying the epidermis layer;

providing, through the first opening, the injectate with the first fluid jet to the underlying one of the plurality of tissue layers underlying the epidermis layer; and extracting, through the second opening, at least a portion of the injectate and the biospecimen from the underlying one of the layers using the second fluid jet.

* * * * *